US012662656B2

(12) United States Patent
Ni et al.

(10) Patent No.: US 12,662,656 B2
(45) Date of Patent: Jun. 23, 2026

(54) LACTICASEIBACILLUS PARACASEI FMBL L23249 FJX AND USE THEREOF

(71) Applicant: SHIHEZI UNIVERSITY, Shihezi City (CN)

(72) Inventors: Yongqing Ni, Shihezi City (CN); Hailong Sun, Shihezi City (CN); Baolong Luo, Shihezi City (CN); Lili Huang, Shihezi City (CN)

(73) Assignee: SHIHEZI UNIVERSITY, Shihezi City (CN)

( * ) Notice: Subject to any disclaimer, the term of this patent is extended or adjusted under 35 U.S.C. 154(b) by 0 days.

(21) Appl. No.: 19/211,374

(22) Filed: May 19, 2025

(65) Prior Publication Data

US 2025/0277185 A1     Sep. 4, 2025

Related U.S. Application Data

(63) Continuation of application No. PCT/CN2024/130108, filed on Nov. 6, 2024.

(30) Foreign Application Priority Data

Nov. 7, 2023     (CN) .......................... 202311470567.0
Aug. 21, 2024     (CN) .......................... 202411150823.2

(51) Int. Cl.
| | |
|---|---|
| *C12N 1/205* | (2026.01) |
| *A23C 9/123* | (2006.01) |
| *A23C 11/10* | (2025.01) |
| *A61K 35/00* | (2006.01) |
| *A61P 39/00* | (2006.01) |

(52) U.S. Cl.
CPC ............ *C12N 1/205* (2021.05); *A23C 9/1234* (2013.01); *A23C 11/106* (2013.01); *A61P 39/00* (2018.01); *A61K 2035/115* (2013.01)

(58) Field of Classification Search
None
See application file for complete search history.

(56) References Cited

FOREIGN PATENT DOCUMENTS

| | | |
|---|---|---|
| CN | 102613381 A | 8/2012 |
| CN | 110628678 B | 4/2022 |
| CN | 115191559 A | 10/2022 |
| CN | 116709935 A | 9/2023 |
| CN | 118909872 A | 11/2024 |
| KR | 102210223 B1 | 2/2021 |
| WO | 2023140614 A1 | 7/2023 |

OTHER PUBLICATIONS

Zhang et al. "Effects of Fermented Milk Containing Lacticaseibacillus paracasei Strain Shirota on Constipation in Patients with Depression: A Randomized, Double-Blind, Placebo-Controlled Trial". Nutrients, 2021, 12, 2238, pp. 1-16.*

Shangfu Yu et al., In vitro antioxidant activity of ten strains of lactobacillus with sequestering lead ions, Science and Technology of Food Industry, Dec. 31, 2016, Sections 1.1, 2.1, and 2.3 on pp. 254-258, vol. 37, Issue 24, Figure 1 and Figure 3.

Mesquita, M.C. et al., Survival of Lactobacillus paracasei subsp. paracasei LBC 81 in Fermented Beverage from Chickpeas and Coconut in a Static In Vitro Digestion Model, Fermentation, Jul. 28, 2021, pp. 1-11, vol. 7, Literature No. 135.

International Search Report of PCT Patent Application No. PCT/CN2024/130108 issued on Feb. 12, 2025.

Written Opinion of the International Searching Authority of PCT Patent Application No. PCT/CN2024/130108 issued on Feb. 12, 2025.

* cited by examiner

*Primary Examiner* — Vera Afremova

(57)     ABSTRACT

The present disclosure provides a *Lacticaseibacillus paracasei* FMBL L23249 FJX and uses thereof. The *Lacticaseibacillus paracasei* FMBL L23249 FJX was deposited on 26 Jun. 2023 at China Center for Type Culture Collection (CCTCC) under accession number CCTCC NO: M 20231097. The *Lacticaseibacillus paracasei* FMBL L23249 FJX is capable of achieving rapid proliferation utilizing a *Cicer arietinum* L. leach liquor, used for preparing *Cicer arietinum* L. yogurt, is also capable of adsorbing heavy metals, or used in the preparation of drugs, food, health products or cosmetics for preventing or treating heavy metal poisoning. The *Lacticaseibacillus paracasei* FMBL L23249 FJX has high adsorptivity on metals lead and cadmium, i.e., a lead adsorption rate is as high as 99.87%, and a cadmium adsorption rate is 82.74%. The *Lacticaseibacillus paracasei* FMBL L23249 FJX has good acid and bile salt resistance, drug resistance, self-aggregation and hydrophobicity.

2 Claims, 4 Drawing Sheets

Specification includes a Sequence Listing.

SEQUENCE LISTING

```
Sequence total quantity: 2
SEQ ID NO: 1          moltype = DNA  length = 20
FEATURE               Location/Qualifiers
source                1..20
                      mol_type = other DNA
                      organism = synthetic construct
SEQUENCE: 1
gcyggtgcwa acccngttgg                                          20

SEQ ID NO: 2          moltype = DNA  length = 20
FEATURE               Location/Qualifiers
source                1..20
                      mol_type = other DNA
                      organism = synthetic construct
SEQUENCE: 2
aangtnccvc gvatcttgtt                                          20
```

1

LACTICASEIBACILLUS PARACASEI FMBL L23249 FJX AND USE THEREOF

CROSS-REFERENCE TO RELATED APPLICATIONS

This application is a continuation of International Application No. PCT/CN2024/130108, filed on Nov. 6, 2024, which claims priorities to Chinese Patent Application No. 202311470567.0, filed on Nov. 7, 2023, and Chinese Patent Application No. 202411150823.2, filed on Aug. 21, 2024. All of the aforementioned applications are incorporated herein by reference in their entireties.

REFERENCE TO SEQUENCE LISTING

This application includes a Sequence Listing filed electronically as an XML file named "Sequence listing_ERICL-25006-USPT.xml", created on May 7, 2025, with a size of 2,869 bytes. The Sequence Listing is incorporated herein by reference.

TECHNICAL FIELD

The present disclosure belongs to the technical field of microorganisms, and particularly relates to a *Lacticaseibacillus paracasei* FMBL L23249 FJX and use thereof.

BACKGROUND

*Cicer arietinum L.* is a bean with a high nutritional value, which is a special agricultural product from Mulei County, Xinjiang, and contains various bioactive substances. For example, *Cicer arietinum L.* contains about 5.89%-10.1% of galacto-oligosaccharide which is a good source of natural prebiotics, and is capable of stimulating the growth proliferation of probiotics and activating a metabolic function; a *Cicer arietinum L.* protein has the characteristics of high bioavailability, low sensitization and the like, some of *Cicer arietinum L.* polypeptides formed by hydrolysis with microorganism proteases have a good antibacterial function; *Cicer arietinum L.* also contains multivitamins and minerals, thereby meeting daily nutritional needs of the human body. The fermentation of a *Cicer arietinum L.* leach liquor with probiotics not only enhances the activity of probiotics, but also further increases postbiotics and active substances generated by probiotic metabolism on the basis of nutritional substances and active ingredients of *Cicer arietinum L.* milk itself while endowing *Cicer arietinum L.* with unique flavor so as to improve the unfavorable flavor of *Cicer arietinum L.* For example, invention patent CN102613381A discloses fermentation of probiotic peptides with probiotics and *Cicer arietinum L.*; invention patent CN115191559A discloses a preparation method of a *Cicer arietinum L.* soybean milk fermented beverage by which the obtained *Cicer arietinum L.* soybean milk fermented beverage has a significantly increased antioxidant ability, a DPPH free radical clearance ability, an ABTS+ free radical clearance ability, fluctuated functional indicators and reduced protein and fat indicators, and is capable of adapting to more populations such as people with obesity, hypertension, hyperlipidemia and hyperglycemia. However, the ability of probiotics to perform fermentation utilizing the *Cicer arietinum L.* leach liquor has strain specificity. There are differences between the abilities of different strains to utilize the *Cicer arietinum L.* leach liquor.

A heavy metal is an element with large density and high atom mass, and has non-biodegradability. If the heavy metal is absorbed by a human body or other animals and plants, it will harm the healthy growth of the human body and other animals and plants. Lead is the second largest excess heavy metal found in the world, which enters the human body through food (65%), water (20%) and air (15%), thereby leading to neurological dysfunction, renal disorders and the like. Cadmium is mainly caused by human activities, metal smelting, chemical fuel combustion and sewage sludge; cadmium has relatively large toxicity, and cadmium poisoning generates various harmful effects on cell molecules mainly through oxidation-antioxidation imbalance, thereby leading to the occurrence of hypertension, renal tubular dysfunction, fractures and cancers. Too high cadmium content severely impairs nervous systems, hematopoietic systems, liver functions, reproductive functions and the like of livestocks and poultries. At present, methods for removing heavy metals from a polluted system comprise a physical repair method, a chemical precipitation method, a dialysis method, an ion exchange method, a reverse osmosis method, a solvent extraction method and the like. However, most of these methods are high in cost and cause harm to environments. A biological method becomes a research hotspot for removal of heavy metal pollution due to its advantages of high efficiency, no toxicity, environmental protection, economic benefits and the like. In the biological method, bacteria, fungi, yeast and the like are mainly used as adsorbents to adsorb heavy metals. For example, invention patent CN110628678B discloses a heavy metal resisting cupriavidus which is capable of resisting heavy metal copper, improving the germination rate of seeds polluted by $Cu^{2+}$, promoting the growth of seedlings polluted by $Cu^{2+}$ and effectively removing copper ions in the environment, is used as a formulation for remediation of soil polluted by $Cu^{2+}$, but is not used for heavy metal poisoning of the human body or other animals.

*Lacticaseibacillus paracasei* is a class of microorganisms that have beneficial activity to the human body. *Lacticaseibacillus paracasei* is colonized in a human intestinal tract to promote flora balance in the intestinal tract and release active substances to affect the physiological metabolism of the human body, so as to facilitate the health of a host. More and more evidences prove that metabolites generated when plant derived food is fermented by *Lacticaseibacillus paracasei*, such as short-chain fatty acids, bacteriocins, vitamins and trimethylamine, are capable of triggering the probiotic effect of an organism.

During the research, a *Lacticaseibacillus paracasei* FMBL L23249 FJX is isolated from the human intestinal tract by the inventor, the *Lacticaseibacillus paracasei* FMBL L23249 FJX is capable of achieving rapid proliferation by efficiently utilizing *Cicer arietinum L.* leach liquor, and therefore is more suitable for a *Cicer arietinum L.* leach liquor system. After 12 h of fermentation, the viable count of the *Lacticaseibacillus paracasei* FMBL L23249 FJX reaches 9.17±0.01 1 g (CFU/mL). After storage for 21 d at 4° C., the viable count of the *Lacticaseibacillus paracasei* FMBL L23249 FJX in the *Cicer arietinum L.* leach liquor is still maintained as more than 8.32±0.03 1 g (CFU/mL), and therefore the *Lacticaseibacillus paracasei* FMBL L23249 FJX is used for preparation of yogurt. Then, it is unexpectedly found that the *Lacticaseibacillus paracasei* FMBL L23249 FJX has relatively high adsorptivity on heavy metals lead and cadmium, has good resistance at a lead ion concentration of 0-300 mg/L, and is still alive at a cadmium ion concentration of 300 mg/L. Furthermore, the *Lactica-*

US 12,662,656 B2

3

*seibacillus paracasei* FMBL L23249 FJX has acid and bile salt resistance, an antioxidant ability, an bacteriostatic property and other effects. The *Lacticaseibacillus paracasei* FMBL L23249 FJX is used for preparing adsorbents that adsorb heavy metals lead and cadmium, drugs for relieving lead and/or cadmium poisoning and inhibiting pathogenic bacteria, fermented food, health products, food additives and feeds or microbial formulations and the like, and has wide application prospects.

SUMMARY

The first objective of the present disclosure is to provide a *Lacticaseibacillus paracasei* FMBL L23249 FJX, wherein the *Lacticaseibacillus paracasei* FMBL L23249 FJX was deposited on Jun. 26, 2023 at China Center for Type Culture Collection (CCTCC) under accession number CCTCC NO: M 20231097.

The second objective of the present disclosure is to provide a microbial inoculum, comprising the *Lacticaseibacillus paracasei* FMBL L23249 FJX or a fermentation broth thereof.

The third objective of the present disclosure is to provide a ferment, comprising the *Lacticaseibacillus paracasei* FMBL L23249 FJX.

The fourth objective of the present disclosure is to provide use of the *Lacticaseibacillus paracasei* FMBL L23249 FJX, the microbial inoculum or the ferment in the preparation of starter cultures, fermented food, health products, food additives or dietary supplements.

Preferably, the fermented products are fermented dairy products or plant-based fermented beverages.

Preferably, the fermented dairy products are fermented milk, fermented milk beverages containing active probiotics or non-active fermented milk beverages.

Preferably, the fermented milk is yogurt or cheese.

The fifth objective of the present disclosure is to provide use of the *Lacticaseibacillus paracasei* FMBL L23249 FJX, the microbial inoculum or the ferment in removal of heavy metals.

The sixth objective of the present disclosure is to provide use of the *Lacticaseibacillus paracasei* FMBL L23249 FJX, the microbial inoculum or the ferment in the preparation of drugs, health products or cosmetics for preventing or treating heavy metal poisoning.

Preferably, the heavy metal poisoning is chronic heavy metal poisoning.

Preferably, the heavy metals are cadmium and/or lead.

The seventh objective of the present disclosure is to provide use of the *Lacticaseibacillus paracasei* FMBL L23249 FJX, the microbial inoculum or the ferment in the preparation of antioxidant products.

The eighth objective of the present disclosure is to provide use of the *Lacticaseibacillus paracasei* FMBL L23249 FJX, the microbial inoculum or the ferment in the preparation of bacteriostatic products.

The ninth objective of the present disclosure is to provide a dairy product, which is prepared by using the *Lacticaseibacillus paracasei* FMBL L23249 FJX, the microbial inoculum or the ferment.

Preferably, the dairy product is soybean yogurt, pea yogurt, *Cicer arietinum L.* yogurt, kidney bean yogurt, or black bean yogurt.

Preferably, the dairy product is the *Cicer arietinum L.* yogurt.

The present disclosure has the beneficial effects: the present disclosure provides a *Lacticaseibacillus paracasei*

4

FMBL L23249 FJX which is suitable for fermentation of *Cicer arietinum L.*, the *Lacticaseibacillus paracasei* FMBL L23249 FJX was deposited on 26 Jun. 2023 at CCTCC under accession number CCTCC NO: M 20231097; the viable count of the *Lacticaseibacillus paracasei* FMBL L23249 FJX reaches 8.79±0.01 1 g (CFU/mL) after 8 h of fermentation, and is balanced in 9.17±0.01 1 g (CFU/mL) after 12 h of fermentation; and the rapid proliferation of the *Lacticaseibacillus paracasei* FMBL L23249 FJX is achieved by efficiently utilizing the *Cicer arietinum L.* leach liquor. After 16 h of fermentation, the *Lacticaseibacillus paracasei* FMBL L23249 FJX has a pH value of 3.76 and a titratable acidity 56 T°; and the *Lacticaseibacillus paracasei* FMBL L23249 FJX is more suitable for a *Cicer arietinum L.* leach liquor system. After 12 h of fermentation, the viable count of the *Lacticaseibacillus paracasei* FMBL L23249 FJX reaches 9.17±0.01 1 g (CFU/mL), the viable count of the *Lacticaseibacillus paracasei* FMBL L23249 FJX in the *Cicer arietinum L.* leach liquor is still maintained as more than 8.32±0.03 1 g (CFU/mL) after storage for 21 d at 4° C., and therefore the *Lacticaseibacillus paracasei* FMBL L23249 FJX is used for preparing yogurt; the *Lacticaseibacillus paracasei* FMBL L23249 FJX is used for heavy metal adsorption or in the preparation of drugs, food, health products or cosmetics for preventing or treating heavy metal poisoning, and the *Lacticaseibacillus plantarum* has a strong lead and cadmium adsorption ability, i.e., the lead adsorption rate reaches 99.87% and the cadmium adsorption rate is 82.74%; the *Lacticaseibacillus paracasei* FMBL L23249 FJX has good resistance at the lead ion concentration of 0-300 mg/L, and still survives at the cadmium ion concentration of 300 mg/L; the *Lacticaseibacillus paracasei* FMBL L23249 FJX has an inhibitory effect on diarrheogenic *Escherichia coli*, enterotoxigenic *Escherichia coli*, enterohemorrhage *Escherichia coli* and *Listeria monocytogenes*; the *Lacticaseibacillus paracasei* FMBL L23249 FJX has acid resistance and bile salt resistance; the *Lacticaseibacillus paracasei* FMBL L23249 FJX has a carbohydrate utilizing ability and a good antioxidant ability, is used for preparing adsorbents for adsorbing heavy metals lead and cadmium, drugs for relieving lead and/cadmium toxicity and inhibiting pathogenic bacteria, fermented food, health products, food additives and feeds or microbial formulations and the like, and has wide application prospects.

BRIEF DESCRIPTION OF THE DRAWINGS

In order to more clearly illustrate the technical solutions of the embodiments of the present disclosure, a brief introduction will be given to the accompanying drawings required for the embodiments. It should be understood that the following drawings only illustrate certain embodiments of the present disclosure and therefore should not be regarded as limiting the scope. For those of ordinary skill in the art, other related drawings can also be obtained based on these drawings without making creative efforts.

5

Figure 4:
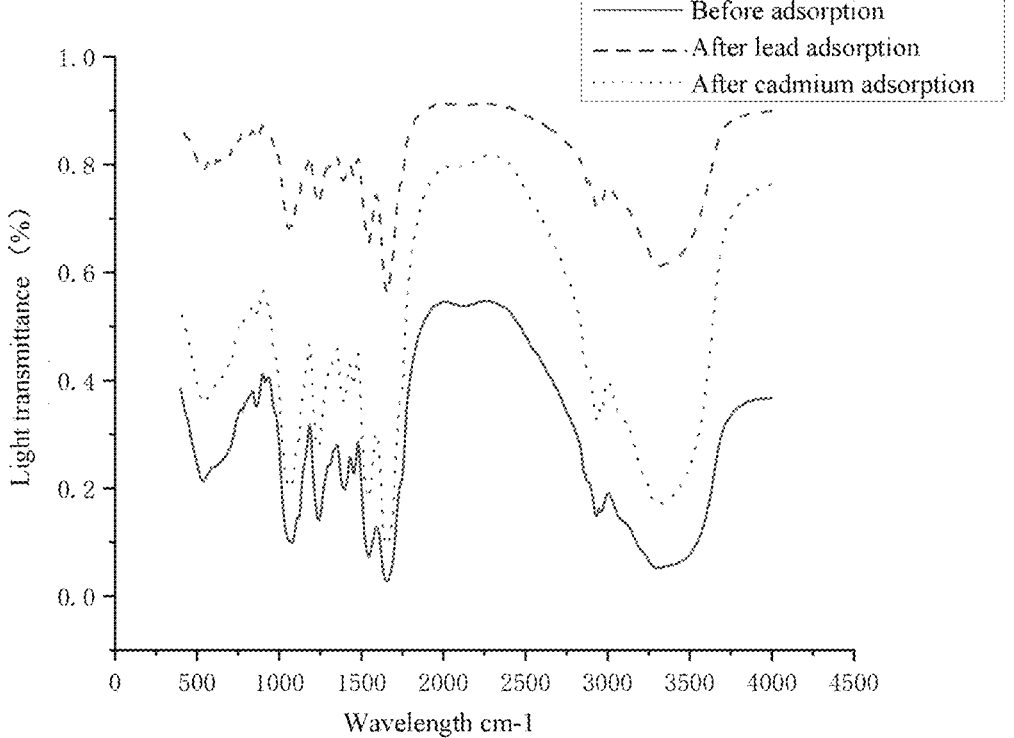

FIG. 4 shows the infrared spectroscopy scanning absorption spectra before adsorption by strain FMBL L23249 FJX, the lead absorption spectrum after adsorption, and the calcium absorption spectrum after adsorption.

DETAILED DESCRIPTION OF THE EMBODIMENTS

Next, specific embodiments of the present disclosure will be described in detail through several embodiments to further explain the present disclosure, but are not intended to limit the claims of the present disclosure.

*Cicer arietinum L.* in the following embodiments is commercially available.

*Lacticaseibacillus paracasei* CGMCC1.2345 is purchased from China General Microbiological Culture Collection Center; *Lacticaseibacillus paracasei* FMBL L23249 FJX and other control strains are isolated by researchers from the Food Microbiology and Biotechnology Research Center at the School of Food Science, Shihezi University from feces of healthy individuals and stored in a lab.

In the following embodiments, the LAMVAB agar culture medium formulation is as follows: 10.0 g of peptone, 8.0 g of beef extract, 4.0 g of yeast extract, 20.0 g of glucose, 1.0 mL of Tween 80, 2.0 g of $K_2HPO_4$, 5.0 g of sodium acetate, 2.0 g of diammonium hydrogen citrate, 0.2 g of $MgSO_4 \cdot 7H_2O$, 0.05 g of $MnSO_4 \cdot 4H_2O$, 0.05g of bromocresol green, 18.0 g of agar, 0.5 g of L-cysteine hydrochloride and 20.0 mg of vancomycin, and pH 5.0.

DeMan, Rogosa and Sharpe (MRS) liquid culture medium: 10 g of peptone, 10 g of beef extract, 5 g of yeast extract, 20 g of glucose, 1 mL of Tween 80, 2 g of $K_2HPO_4$, 5 g of sodium acetate, 2 g of diammonium hydrogen citrate, 0.58 g of $MgSO_4 \cdot 7H_2O$, 0.25 g of $MnSO_4 \cdot 4H_2O$, and 1000 mL of deionized water;

M17 broth culture medium; M17 solid culture medium (M17 broth culture medium plus 2% agar);

Yeast extract, peptone and glucose (PYG) culture medium: 10.0 g of peptone, 5.0 g of yeast extract, 1.0 g of glucose, 20.0 g of agar, and 1000 mL of deionized water;

Tryptone soy agar (TSA) culture medium: 15.0 g of tryptone, 5.0 g of soy peptone, 5.0 g of sodium chloride, 15 g of agar, and 1000 mL of deionized water; and Nutrient broth agar culture medium: 5.0 g of peptone, 3.0 g of beef extract, 5.0 g of sodium chloride, 20.0 g of agar, and 1000 mL of deionized water.

Embodiment 1 Isolation and Identification of Strain

Fresh fecal samples were collected from healthy Uyghur population in Aksu, Xinjiang into a sterile fecal collection tube, stored in a vehicle-mounted refrigerator at −18° C. to −15° C., and transported back to a lab within 12 h. Strains were isolated and purified by using a gradient dilution coating plate method.

1.0 g of fecal was weighed into 9.0 mL of normal saline solution for gradient dilution in sequence. 0.1 mL of fecal sample dilution solution was taken, evenly coated onto an LAMVAB agar culture medium, and then subjected to anaerobic culture for 24-36 h at 37° C. According to colony characteristics, suspected *Lacticaseibacillus* colonies with yellow or faint yellow transparent circles around were randomly picked and purified three times, strains that were gram-positive, catalase-negative and had rod-like cellular morphology were initially screened in combination with gram staining and a hydrogen peroxide catalase experiment, and the above strains were enriched to prepare a bacterial suspension.

The DNA of strains was extracted by utilizing a bacterial genome DNA rapid extract kit, and the extracted DNA was amplified using groEL gene primers:

```
GroEL-Lac-F (SEQ ID NO. 1):
5'-GCY GGT GCW AAC CCN GTT GG-3'

GroEL-Lac-R (SEQ ID NO. 2):
5'-AAN GTN CCV CGV ATC TTG TT-3'.
```

The amplified products were transferred to Suzhou Jinweizhi Biotechnology Co., Ltd for sequencing after quality inspection. The obtained sequences were submitted to GenBank database for BLAST online alignment.

Figure 1:
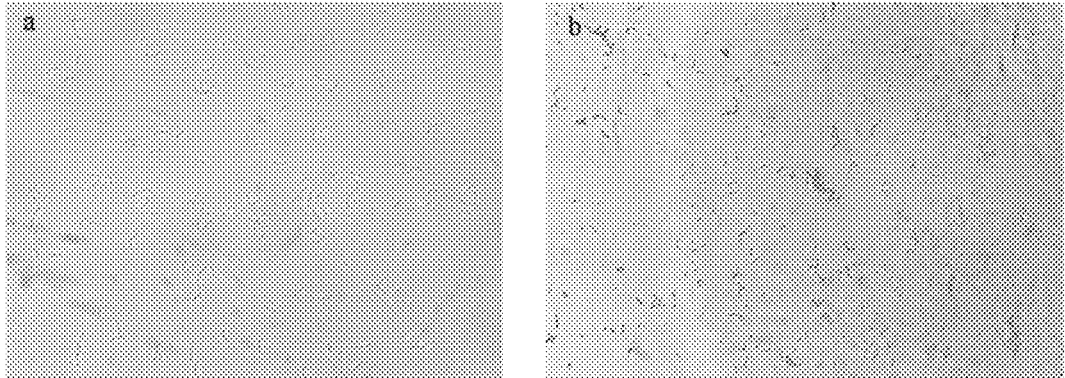
FIG. 1 shows colony and microscopic characteristics of the microbial strain FMBL L23249 FJX, wherein a of FIG. 1 depicts the colony morphology of strain FMBL L23249 FJX, b of FIG. 1 provides microscopic observations of the strain FMBL L23249 FJX.
Figure 2:
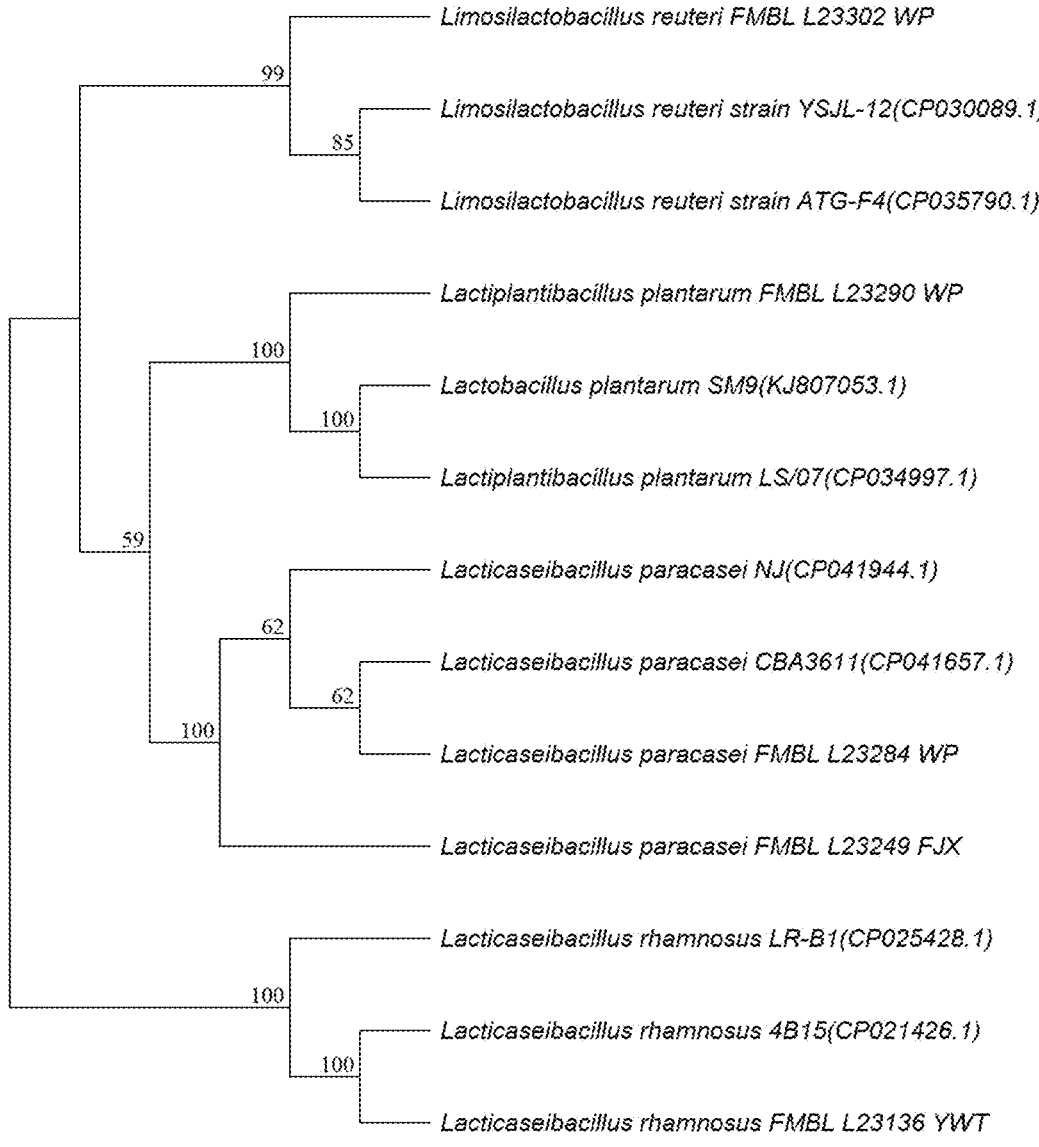
FIG. 2 shows the phylogenetic tree of strain FMBL L23249 FJX.

The colony characteristics and microscopic characteristics of the strain FMBL L23249 FJX are as shown in FIG. 1, and a phylogenetic tree is as shown in FIG. 2. The strain FMBL L23249 FJX obtained by isolation and identification belongs to *Lacticaseibacillus paracasei* (Latin name), named *Lacticaseibacillus paracasei* FMBLL23249 FJX, which was deposited on 26 Jun. 2023 at CCTCC under accession number CCTCC NO: M 20231097, the address: WuHan University of China, Tel: 027-68754052, and fax: 027-68754833.

In the following embodiments, *Lacticaseibacillus paracasei* FMBL L23249 FJX is abbreviated as *Lacticaseibacillus paracasei* FMBL L23249 FJX.

Embodiment 2 Preparation of *Cicer arietinum L.* Leach Liquor

The preparation method of the *Cicer arietinum L.* leach liquor is as follows:

(1) 100 g of *Cicer arietinum L.* was weighed to ensure no pest and disease mechanical injury. The weighed *Cicer arietinum L.* was repeatedly rinsed with running water to clean sludge and impurities on the surface of the *Cicer arietinum L.*, and then dried for later use.

(2) The above washed *Cicer arietinum L.* was added into 300 mL of drinking water to be soaked for 12 h at room temperature so that *Cicer arietinum L.* particles were naturally enlarged and in a semi-germinating state, and then filtered to discard water for soaking the *Cicer arietinum L.*, and subsequently the semi-germinated *Cicer arietinum L.* was drained off for later use.

(3) 600 ml of 60° C. drinking water and 0.45% α-amylase (1000 μ/g) were added into the semi-germinated *Cicer arietinum L.*, and then the above *Cicer arietinum L.* was ground for 8 min and underwent enzymolysis for 24 min at 60° C.

(4) The *Cicer arietinum L.* homogenate obtained after enzymolysis was boiled for 5 min, passed through 100-mesh filter cloth after being cooled, and then sub-packaged to obtain the *Cicer arietinum L.* leach liquor.

(5) The *Cicer arietinum L.* leach liquor obtained in (4) as described above was sterilized for 10 min at 105° C., then cooled to room temperature and finally stored in a refrigerator at 4° C. for later use.

Embodiment 3 Viable Count of *Lacticaseibacillus paracasei* FMBL L23249 FJX

*Lacticaseibacillus paracasei* FMBL L23249 FJX and other control strains were activated and subcultured for 2-3 generations, then seed cultures were centrifuged to remove the fermented supernatant, bacterial pellets were washed with sterile saline solution, resuspended in sterile saline solution, and then inoculated into the *Cicer arietinum L.* leach liquor in an inoculation amount that a final concentration was $1.0 \times 10^7$ CFU/mL under sterile conditions, and subsequently the inoculated *Cicer arietinum L.* leach liquor was fermented in a constant-temperature incubator at 37° C. 1 mL of samples were taken from the *Cicer arietinum L.* leach liquor at 8 h, 10 h, 12 h and 16 h after fermentation respectively for viable count. Specific data are shown in Table 1 and Table 2.

TABLE 1

Compositions of strains in experiment groups and control groups

| Group | Strain name |
|---|---|
| Experiment group 1 | *Lacticaseibacillus paracasei* FMBL L23249 FJX |
| Control group 1 | *Lacticaseibacillus paracasei* CGMCC1.2345 |

TABLE 1-continued

Compositions of strains in experiment groups and control groups

| Group | Strain name |
|---|---|
| Control group 2 | *Lacticaseibacillus paracasei* FMBL L23601 |
| Control group 3 | *Lacticaseibacillus paracasei* FMBL L23602 |
| Control group 4 | *Lacticaseibacillus paracasei* FMBL L23603 |
| Control group 5 | *Lacticaseibacillus paracasei* FMBL L23604 |
| Control group 6 | *Lacticaseibacillus paracasei* FMBL L23605 |
| Control group 7 | *Lacticaseibacillus paracasei* FMBL L23606 |
| Control group 8 | *Lacticaseibacillus paracasei* FMBL L23607 |
| Control group 9 | *Lacticaseibacillus paracasei* FMBL L23608 |
| Control group 10 | *Lacticaseibacillus paracasei* FMBL L23609 |
| Control group 11 | *Lacticaseibacillus paracasei* FMBL L23610 |
| Control group 12 | *Lacticaseibacillus paracasei* FMBL L23611 |
| Control group 13 | *Lacticaseibacillus paracasei* FMBL L23612 |
| Control group 14 | *Lacticaseibacillus paracasei* FMBL L23614 |
| Control group 15 | *Lacticaseibacillus paracasei* FMBL L23615 |

TABLE 2

Change (lg(CFU/mL)) in viable count of *Lacticaseibacillus paracasei* FMBL L23249 FJX in the process of fermenting *Cicer arietinum L.* leach liquor

| Group | 0 h | 8 h | 10 h | 12 h | 16 h |
|---|---|---|---|---|---|
| Experiment group 1 | 6.99 ± 0.01[d] | 8.79 ± 0.01[c] | 9.08 ± 0.01[b] | 9.17 ± 0.01[a] | 9.17 ± 0.01[a] |
| Control group 1 | 7.01 ± 0.01[c] | 8.57 ± 0.01[b] | 8.65 ± 0.01[a] | 8.63 ± 0.02[a] | 8.65 ± 0.01[a] |
| Control group 2 | 7.00 ± 0.01[b] | 8.34 ± 0.04[a] | 8.38 ± 0.03[a] | 8.36 ± 0.01[a] | 8.34 ± 0.01[a] |
| Control group 3 | 6.99 ± 0.01[d] | 8.00 ± 0.03[c] | 8.26 ± 0.01[b] | 8.40 ± 0.04[a] | 8.39 ± 0.01[a] |
| Control group 4 | 7.00 ± 0.02[d] | 7.91 ± 0.02[c] | 8.08 ± 0.01[b] | 8.18 ± 0.02[a] | 8.18 ± 0.01[a] |
| Control group 5 | 7.00 ± 0.01[d] | 8.24 ± 0.02[c] | 8.42 ± 0.02[b] | 8.53 ± 0.04[a] | 8.51 ± 0.03[a] |
| Control group 6 | 6.99 ± 0.01[d] | 8.11 ± 0.01[c] | 8.27 ± 0.01[b] | 8.37 ± 0.05[a] | 8.37 ± 0.07[a] |
| Control group 7 | 7.00 ± 0.00[d] | 8.56 ± 0.03[c] | 8.62 ± 0.01[b] | 8.66 ± 0.01[a] | 8.65 ± 0.01[ab] |
| Control group 8 | 7.02 ± 0.02[d] | 8.57 ± 0.02[c] | 8.73 ± 0.02[b] | 8.81 ± 0.02[a] | 8.81 ± 0.01[a] |
| Control group 9 | 6.99 ± 0.02[c] | 8.33 ± 0.03[b] | 8.52 ± 0.03[a] | 8.57 ± 0.04[a] | 8.56 ± 0.03[a] |
| Control group 10 | 6.99 ± 0.02[d] | 8.18 ± 0.01[c] | 8.27 ± 0.01[b] | 8.36 ± 0.03[a] | 8.38 ± 0.06[a] |
| Control group 11 | 7.01 ± 0.01[d] | 8.20 ± 0.01[c] | 8.38 ± 0.03[b] | 8.58 ± 0.09[a] | 8.47 ± 0.02[a] |
| Control group 12 | 6.99 ± 0.01[d] | 8.81 ± 0.02[a] | 7.91 ± 0.01[c] | 7.99 ± 0.01[b] | 8.01 ± 0.01[b] |
| Control group 13 | 6.99 ± 0.01[c] | 8.80 ± 0.02[a] | 8.02 ± 0.02[b] | 7.95 ± 0.01[b] | 7.95 ± 0.01[b] |
| Control group 14 | 6.97 ± 0.02[b] | 8.04 ± 0.04[a] | 8.14 ± 0.01[a] | 8.14 ± 0.01[a] | 8.11 ± 0.03[a] |
| Control group 15 | 7.00 ± 0.01[c] | 8.43 ± 0.03[b] | 8.54 ± 0.03[a] | 8.57 ± 0.02[a] | 8.56 ± 0.04[a] |

Note:
there is a significant difference between different letters in the same row and the same line.

It can be seen from Table 2 that after 8 h of fermentation, the viable count of the *Lacticaseibacillus paracasei* FMBL L23249 FJX reached 8.79±0.01 1 g (CFU/mL); and after 12 h of fermentation, the viable count of the *Lacticaseibacillus paracasei* FMBL L23249 FJX was balanced as 9.17±0.01 1 g (CFU/mL). However, after 16 h of fermentation for control group *Lacticaseibacillus paracasei*, the viable count of the *Lacticaseibacillus paracasei* in control group 8 having the highest viable count only reached 8.81±0.01 1g (CFU/mL). Therefore, the *Lacticaseibacillus paracasei* FMBL L23249 FJX was capable of achieving rapid proliferation by efficiently utilizing the *Cicer arietinum L.* leach liquor.

Embodiment 4 pH Value and Titratable Acidity of *Lacticaseibacillus paracasei* FMBL L23249 FJX

*Lacticaseibacillus paracasei* FMBL L23249 FJX and control strains were activated and subcultured for 2-3 generations, then seed cultures were centrifuged to remove the fermented supernatant, bacterial pellets were washed with sterile saline solution, resuspended in sterile saline solution, and then inoculated into the *Cicer arietinum L.* leach liquor in an inoculation amount that a final concentration was $1.0\times10^7$ CFU/mL under sterile conditions, and subsequently the inoculated *Cicer arietinum L.* leach liquor was fermented in a constant-temperature incubator at 37° C. 10 mL of samples were taken from the *Cicer arietinum L.* leach liquor at 8 h, 10 h, 12 h and 16 h after fermentation respectively for determination of pH values and titratable acidities. The results are shown in Table 3 and Table 4.

TABLE 3

Changes in pH value and titratable acidity of *Lacticaseibacillus paracasei* FMBL L23249 FJX in the process of fermenting *Cicer arietinum L.* leach liquor

| Time/h | 8 h | 10 h | 12 h | 16 h |
|---|---|---|---|---|
| pH value | $4.48 \pm 0.02^a$ | $4.05 \pm 0.01^b$ | $3.82 \pm 0.01^c$ | $3.76 \pm 0.01^d$ |
| Titratable acidity/T ° | $34 \pm 1^c$ | $40 \pm 2^b$ | $48 \pm 1^a$ | $56 \pm 2^a$ |

Note:
there is a significant difference between different letters in the same row.

TABLE 4

Changes in pH value and titratable acidity of *Lacticaseibacillus paracasei* CGMCC1.2345 in the process of fermenting *Cicer arietinum L.* leach liquor

| Time/h | 8 h | 10 h | 12 h | 16 h |
|---|---|---|---|---|
| pH value | $4.76 \pm 0.01^a$ | $4.27 \pm 0.01^b$ | $4.01 \pm 0.02^c$ | $3.93 \pm 0.01^d$ |
| Titratable acidity/T ° | $32 \pm 2^d$ | $36 \pm 1^c$ | $40 \pm 1^b$ | $42 \pm 2^a$ |

Note:
there is a significant difference between different letters in the same row.

It can be seen by comparing Table 3 with Table 4 that after 16 h of fermentation, the *Lacticaseibacillus paracasei* FMBL L23249 FJX has a pH value of 3.76 and a titratable acidity of 56 T°; and after 16 h of fermentation, the *Lacticaseibacillus paracasei* CGMCC 1.2345 has a pH value of 3.93 and a titratable acidity of 42 T°. Both the *Lacticaseibacillus paracasei* FMBL L23249 FJX and the *Lacticaseibacillus paracasei* CGMCC 1.2345 meet the acidity requirements for the fermented beverages. Furthermore, in the same range of titratable acidity, the viable count of the *Lacticaseibacillus paracasei* FMBL L23249 FJX is far higher than that of the *Lacticaseibacillus paracasei* CGMCC 1.2345; it can be seen in combination with embodiment 2 that the *Lacticaseibacillus paracasei* FMBL L23249 FJX is more suitable for the *Cicer arietinum L.* leach liquor system.

Embodiment 5 Changes in Viable Count and pH Value of *Lacticaseibacillus paracasei* FMBL L23249 FJX during Storage

*Lacticaseibacillus paracasei* FMBL L23249 FJX and a control strain *Lacticaseibacillus paracasei* CGMCC1.2345 were activated and subcultured for 2-3 generations, then seed cultures were centrifuged to remove the fermented supernatant, bacterial pellets were washed with sterile saline solution, resuspended in sterile saline solution, and then inoculated into the *Cicer arietinum L.* leach liquor in an inoculation amount that a final concentration was $1.0\times10^7$ CFU/mL under sterile conditions, and subsequently the inoculated *Cicer arietinum L.* leach liquor was fermented in a constant-temperature incubator at 37° C. 10 mL of samples were taken from the *Cicer arietinum L.* leach liquor at 12 h, 7 d, 14 d and 21 d after fermentation respectively for determination of viable counts and pH values.

TABLE 5

Changes in viable count and pH value of *Lacticaseibacillus paracasei* FMBL L23249 FJX in fermented *Cicer arietinum L.* leach liquor during storage

| Time/h | 12 h | 7 d | 14 d | 21 d |
|---|---|---|---|---|
| Viable count lg (CFU/mL) | $9.17 \pm 0.01^a$ | $8.93 \pm 0.02^b$ | $8.93 \pm 0.02^b$ | $8.32 \pm 0.03^d$ |
| pH value | $3.82 \pm 0.01^a$ | $3.65 \pm 0.01^b$ | $3.52 \pm 0.02^c$ | $3.45 \pm 0.01^d$ |

Note:
there is a significant difference between different letters in the same row.

TABLE 6

Changes in viable count and pH value of *Lacticaseibacillus paracasei* CGMCC 1.2345 in fermented *Cicer arietinum L.* leach liquor during storage

| Time/h | 12 h | 7 d | 14 d | 21 d |
|---|---|---|---|---|
| Viable count lg (CFU/mL) | $8.63 \pm 0.02^a$ | $8.41 \pm 0.01^b$ | $7.96 \pm 0.01^c$ | $7.74 \pm 0.02^d$ |
| pH value | $4.01 \pm 0.01^a$ | $3.88 \pm 0.02^b$ | $3.62 \pm 0.01^c$ | $3.48 \pm 0.01^d$ |

Note:
there is a significant difference between different letters in the same row.

It can be seen by comparing Table 5 with Table 6 that by using the preparation method of the present disclosure, the viable count of the *Lacticaseibacillus paracasei* FMBL L23249 FJX after fermenting the *Cicer arietinum L.* leach liquor for 12 h reaches 9.17±0.01 1 g (CFU/mL), and the viable count of the *Lacticaseibacillus paracasei* FMBL L23249 FJX in the *Cicer arietinum L.* leach liquor is still maintained as more than 8.32±0.03 1 g (CFU/mL) after storage for 21 d at 4° C.; and the viable count of the *Lacticaseibacillus paracasei* CGMCC 1.2345 prepared in control group after 12 h of fermentation is only 8.63±0.02 1 g (CFU/mL), and the viable count of the *Lacticaseibacillus paracasei* CGMCC 1.2345 in the *Cicer arietinum L.* leach liquor is only maintained as 7.74±0.02 1 g (CFU/mL) after storage for 21 d at 4° C. After 12 h of fermentation and storage for 21 d, the viable count of the *Lacticaseibacillus paracasei* CGMCC 1.2345 is significantly lower than that of the *Lacticaseibacillus paracasei* FMBL L23249 FJX. Therefore, the *Lacticaseibacillus paracasei* FMBL L23249 FJX is more suitable for preparing *Cicer arietinum L.* yogurt.

Embodiment 6 Adsorption Ability of *Lacticaseibacillus paracasei* FMBL L23249 FJX on Heavy Metals Lead and Cadmium 1. To-be-detected Strains

*Lacticaseibacillus plantarum* FMBL L23290 WP, *Lacticaseibacillus paracasei* FMBL L23249 FJX, *Lacticaseibacillus paracasei* FMBL L23284 WP, *Lacticaseibacillus rhamnosus* FMBL L23136 YWT and *Lacticaseibacillus reuteri* were all isolated from feces of healthy individuals. *Lacticaseibacillus plantarum* FMBL L23290 WP, *Lacticaseibacillus paracasei* FMBL L23284 WP, *Lacticaseibacillus rhamnosus* FMBL L23136 YWT and *Lacticaseibacillus reuteri* were all deposited with Food Microbiology and Biotechnology Research Center, School of Food Science and Technology, Shihezi University.

2. Adsorption Experiment (1) A to-be-detected strain was inoculated into a liquid MRS culture medium, and cultured for 24 h at 37° C. to be activated.

(2) The strain activated in step (1) was centrifuged for 20 min at 4° C. under 8000 rpm, and a thallus precipitate was collected and washed three times with a PBS buffer solution (pH=7.4) to obtain a to-be-detected thallus precipitate.

(3) The to-be-detected thallus precipitate obtained in step (2) was prepared into a 50 g/L bacterial suspension; lead nitrate and cadmium nitrate were prepared into a 50 mg/L lead ion solution and a 50 mg/L cadmium ion solution; the bacterial suspension was respectively added into the 50 mg/L lead ion solution and the 50 mg/L cadmium ion solution so that the final concentrations of thalli in the solutions were 5g/L; the thalli were subjected to shaking culture for 1 h at 37° C. under 150 rpm in a table concentrator and then centrifuged to take supernatants; and the contents of lead and cadmium in the supernatants were measured by an atomic spectrophotometer method. The adsorption rate was calculated by the following formula. $C_0$ is the contents of lead and cadmium ions in the solution before adsorption, and $C_I$ is the contents of lead and cadmium ions in the solution after adsorption.

$$\text{Adsorption rate } (\%) = \frac{C0 - CI}{C0} * 100\%$$

3. Conclusion

Figure 3:
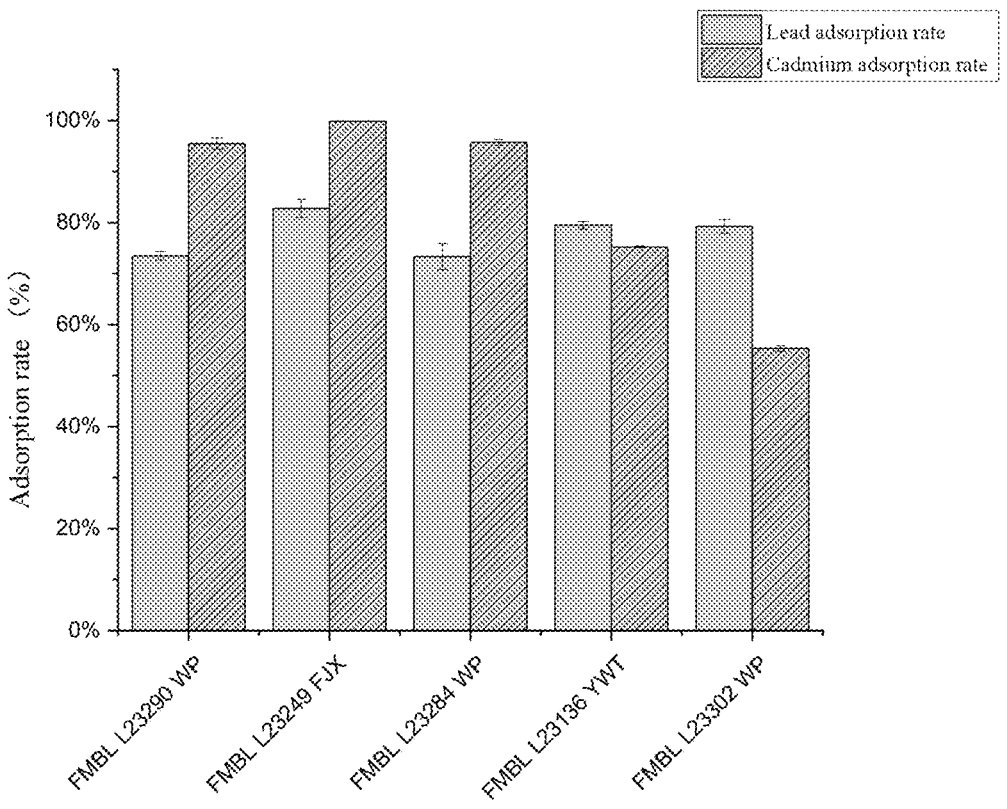
FIG. 3 shows the absorption rates of lead and cadmium by strain FMBL L23290 WP, FMBL L23249 FJX, FMBL L23284 WP, FMBL L23136 YWT, FMBL L23302 WP.

The results are as shown in FIG. 3, indicating that the adsorption rate of each strain on lead is between 55% and 100%, and the adsorption rate of each strain on cadmium is between 70% and 90%. There is a significant difference between the adsorption abilities of different strains on heavy metal ions, wherein, the *Lacticaseibacillus paracasei* FMBL L23249 FJX has the best heavy metal adsorption effect, i.e., the *Lacticaseibacillus paracasei* FMBL L23249 FJX has a lead ion adsorption rate of 99.87% and a cadmium ion adsorption rate of 82.74% which are significantly superior to those of other strains.

Embodiment 7 Effects of Different Concentrations of Lead and Cadmium Ions on Growth of *Lacticaseibacillus paracasei* FMBL L23249 FJX 1. Experimental Process (1) Lead nitrate and cadmium nitrate solutions were filtered using a filter membrane and then added into MRS liquid culture mediums to respectively prepare liquid culture media with lead ion concentrations of (50 mg/L, 100 mg/L, 200 mg/L and 300 mg/L) and cadmium ion concentrations of (50 mg/L, 100 mg/L, 200 mg/L and 300 mg/L).

(2) The activated *Lacticaseibacillus paracasei* FMBL L23249 FJX was added into the liquid culture media prepared in step (1) in an inoculation amount of 2%. After culture for 24 h at 37° C., an OD60 value was measured by using a spectrophotometer, and a liquid culture medium containing no heavy metal ions was used as control.

TABLE 7

| Activity of *Lacticaseibacillus paracasei* FMBL L23249 FJX in cadmium-containing culture medium | | | | | |
| --- | --- | --- | --- | --- | --- |
| | Cadmium ion concentration (OD$_{600}$ value) | | | | |
| | 0 mg/L | 50 mg/L | 100 mg/L | 200 mg/L | 300 mg/L |
| FMBL L23290 WP | $1.58 \pm 0.0468^a$ | $0.24 \pm 0.075^b$ | $0.2 \pm 0.0045^a$ | $0.14 \pm 0.0019^a$ | $0.01 \pm 0.0043^a$ |
| FMBL L23249 FJX | $1.53 \pm 0.0198^a$ | $1.41 \pm 0.012^d$ | $1.37 \pm 0.0047^c$ | $0.83 \pm 0.0374^b$ | $0.25 \pm 0.0506^b$ |
| FMBL L23284 WP | $1.35 \pm 0.0052^b$ | $1.15 \pm 0.0352^c$ | $0.67 \pm 0.1146^b$ | $0.46 \pm 0.0053^a$ | $0.20 \pm 0.0087^b$ |
| FMBL L23136 YWT | $1.43 \pm 0.0323^a$ | $0.03 \pm 0.0076^a$ | $0.12 \pm 0.0048^a$ | $0.12 \pm 0.0076^a$ | $0.01 \pm 0.0025^a$ |
| FMBL L23302 WP | $1.33 \pm 0.0458^b$ | $1.14 \pm 0.0037^c$ | $0.14 \pm 0.0012^a$ | $0.12 \pm 0.0061^a$ | $0.02 \pm 0.0087^a$ |

TABLE 8

Activity of *Lacticaseibacillus paracasei* FMBL L23249 FJX in lead-containing culture medium

| | Lead ion concentration ($OD_{600}$ value) | | | | |
|---|---|---|---|---|---|
| | 0 mg/L | 50 mg/L | 100 mg/L | 200 mg/L | 300 mg/L |
| FMBL L23290 WP | $1.52 \pm 0.0323^c$ | $1.41 \pm 0.0355^c$ | $1.19 \pm 0.0046^b$ | $1.39 \pm 0.0461^c$ | $1.36 \pm 0.0362^c$ |
| FMBL L23249 FJX | $1.52 \pm 0.0319^c$ | $1.49 \pm 0.0043^d$ | $1.46 \pm 0.0084^c$ | $1.45 \pm 0.0042^d$ | $1.45 \pm 0.0143^d$ |
| FMBL L23284 WP | $1.38 \pm 0.0157^b$ | $1.27 \pm 0.0215^b$ | $1.23 \pm 0.0277^b$ | $1.26 \pm 0.0315^b$ | $1.25 \pm 0.0074^b$ |
| FMBL L23136 YWT | $1.39 \pm 0.0437^b$ | $1.37 \pm 0.0554^c$ | $1.21 \pm 0.0394^b$ | $1.34 \pm 0.0445^{bc}$ | $1.31 \pm 0.0097^b$ |
| FMBL L23302 WP | $1.17 \pm 0.0571^a$ | $1.04 \pm 0.2161^a$ | $0.77 \pm 0.3696^a$ | $1.04 \pm 0.2167^a$ | $1.02 \pm 0.2239^a$ |

2. Conclusion

The effect results of different lead and cadmium ion concentrations on growth of *Lacticaseibacillus paracasei* FMBL L23249 FJX are shown in Table 7 and Table 8. When the concentration of lead ions was in a range of 0-300 mg/L, the growth of the *Lacticaseibacillus paracasei* FMBL L23249 FJX was basically not affected, with good resistance. When the concentration of cadmium ions was in a range of 0-100 mg/L, the *Lacticaseibacillus paracasei* FMBL L23249 FJX was basically not affected; when the concentration of cadmium ions was ≥200 mg/L, the growth activity of the *Lacticaseibacillus paracasei* FMBL L23249 FJX was gradually weakened with an increase in cadmium ion concentration, but obviously higher than the growth activities of other strains; when the concentration of cadmium ions was 300 mg/L, the *Lacticaseibacillus paracasei* FMBL L23249 FJX still survived, and had a certain resistance on cadmium ions.

Embodiment 8 Detection of Relevant Groups of
*Lacticaseibacillus paracasei* FMBL L23249 FJX
Adsorbing Lead and Cadmium Ions via Infrared
Spectral Scanning 1. Experimental Process
   (1) Lead nitrate and cadmium nitrate were respectively prepared into a 50 mg/L lead ion solution and a 50 mg/L cadmium ion solution, and the above two solutions were sterilized for later use.
   (2) *Lacticaseibacillus paracasei* FMBL L23249 FJX was activated and then centrifuged to collect thalli, a thallus precipitate was washed three times with a PBS buffer solution and then added into the lead ion solution and cadmium ion solution in step (1), so that the final concentrations of thalli in the solutions were 5 g/L. The thalli were cultured for 1 h at 37° C. under 150 rpm in a table concentrator and then centrifuged to collect the thallus precipitate.
   (3) The thallus precipitate in step (2) was subjected to freeze drying. The dried thallus powders were uniformly mixed with potassium bromide in a ratio of 1:50, ground and compressed into a slice. The slice was determined by a Fourier transform infrared spectroscope. A sample was scanned in a range of 400-4000 $cm^{-1}$ and its spectrum was recorded.

2. Conclusion

The results are as shown in FIG. 4. It can be seen that both spectral peak intensities before and after lead and cadmium stress increase, and the positions of characteristic peaks change, indicating that functional groups such as carbonyl, a phosphate group and hydroxyl on the thalli are related to a heavy metal adsorption ability.

Embodiment 9 Determination of Probiotic
Characteristics of *Lacticaseibacillus paracasei*
FMBL L23249 FJX 1. Acid-resisting and bile salt-resisting ability

*Lacticaseibacillus* activated and cultured for 24 h was centrifuged (1000 rpm, 5 min, and 4° C.) and then a supernatant was discarded, and a thallus precipitate was collected. The collected thallus precipitate was then added into MRS liquid culture media with different pH values (2.5, 3, 3.5 and 4) and different bile salt concentrations (0.05%, 0.1% and 0.5%) and then placed for 0 h and 4 h at 37° C., subsequently sampled and coated, and viable count was performed after 48 h to calculate the viability of the *Lacticaseibacillus* under different pH conditions.

TABLE 9

Determination of acidity resistance of *Lacticaseibacillus paracasei* FMBL L23249 FJX

| Strain | pH = 2.5 | pH = 3 | pH = 3.5 | pH = 4 |
|---|---|---|---|---|
| *Lacticaseibacillus paracasei* FMBL L23249 FJX | 23 ± 1.47% | 29.04 ± 1.22% | 36.45 ± 2.43% | 40.55 ± 1.47% |

TABLE 10

Determination of bile salt resistance of
*Lacticaseibacillus paracasei* FMBL L23249 FJX

| Strain | 0.05% bile salt | 0.1% bile salt | 0.5% bile salt |
|---|---|---|---|
| *Lacticaseibacillus paracasei* FMBL L23249 FJX | 51.64 ± 0.88% | 22.54 ± 1.16% | 1.93 ± 0.33% |

It can be seen from Table 9 and Table 10 that the *Lacticaseibacillus paracasei* FMBL L23249 FJX survived under the conditions of pH 4-pH 2.5. The viability under the condition of pH4 was 40.55±1.47%, and the viability under the condition of pH4 was still more than 23±1.47%; and the viability at the concentration of 0.05% bile salt reached 51.64±0.88%. It indicates that the *Lacticaseibacillus paracasei* FMBL L23249 FJX has good acid and bile salt resistance characteristics, and the good acid and bile salt resistance characteristics enable strains to reach colonization sites so as to survive, grow and take a probiotic effect in a gastrointestinal tract.

2. Bacteriostatic Experiment

The bacteriostatic activity of metabolites of *Lacticaseibacillus plantarum* FMBL L23220 CLL was determined by using an oxford cup method based on diarrheogenic *Escherichia coli* (10411), enterotoxigenic *Escherichia coli* (21530), enterotoxigenic *Escherichia coli* (10421), *Salmonella typhimurium* (10420), *Listeria monocytogenes* (LS1) and *Salmonella enteritidis* (SM1) as indicator bacteria (purchase sources are shown in Table 6). The strains were inoculated into the MRS culture medium in an inoculation amount of 2%, cultured for 24 h at 37° C. and then centrifuged for 10 min under 8000 rpm, and a supernatant was taken, filtered and sterilized to prepare cell-free supernatant. The indicator bacteria were coated onto corresponding solid culture media according to a concentration of $10^6$ CFU/mL, an aseptic oxford cup was vertically placed in a culture dish coated with pathogenic bacteria, and 0.2 mL of cell-free supernatant was added into the oxford cup. The culture dish was diffused for 4 h at 4° C. and then cultured for 24 h in an incubator at 37° C., and a diameter of a bacteriostatic circle was measured.

TABLE 11

Sources of indicator bacteria

| Strain | Source | Collection center number | Culture medium |
|---|---|---|---|
| *Escherichia coil* EPEC O127:K63 | China Center of Industrial Culture Collection | CICC 10411 | Nutrient agar |
| *Escherichia coil* ETEC O78:K80 | China Center of Industrial Culture Collection | CICC 10421 | Nutrient agar |
| *Salmonella enterica* | China Center of Industrial | CICC | Nutrient |

TABLE 11-continued

Sources of indicator bacteria

| Strain | Source | Collection center number | Culture medium |
|---|---|---|---|
| subsp. *enterica* serovar *Typhimurium* | Culture Collection | 10420 | agar |
| *Escherichia coil* EHEC O157:H7 | China Center of Industrial Culture Collection | CICC 21530 | Nutrient agar |
| *Listeria monocytogenes* | China General Microbiological Culture Collection Center | CGMCC 1.9136 | PYG culture medium |
| *Salmonella enterica* subsp. *Enterica* | China General Microbiological Culture Collection Center | CGMCC 1.10754 | TSA culture medium |

TABLE 12

Determination of bacteriostatic ability of
*Lacticaseibacillus paracasei* FMBL L23249 FJX

| Strain | 10411 | 10421 | 21530 | 10420 | LS1 | SM1 |
|---|---|---|---|---|---|---|
| *Lacticaseibacillus paracasei* FMBL L23249 FJX | ++++ | +++ | ++ | + | − | + |

Note:
≤15 +; 15 < a diameter of a bacteriostatic circle ≤20 ++; 20 < a diameter of a bacteriostatic circle ≤25 +++; a diameter of a bacteriostatic circle >25 +++; no bacteriostatic circle −.

It can be seen from Table 12 that the *Lacticaseibacillus paracasei* FMBL L23249 FJX has a good bacteriostatic ability on enteropathogenic *Escherichia coil* (10411), enterotoxigenic *Escherichia coli* (10421), enterohemorrhage *Escherichia coli* (21530), *Salmonella enterica* subsp. *enterica serovar typhimurium* (10420) and *Salmonella enteritidis* (SM1).

3. Drug Sensitivity Test

A disk diffusion method (K-B method) was used, and drug sensitivity disk information is seen in Table 13. The strains were inoculated into a sterilized liquid MRS culture medium in an inoculation amount of 2% and cultured for 24 h at 37° C., the activated strains were diluted and coated (a concentration of thalli was $10^7$-$10^8$ CFU/mL), drug sensitive disks were uniformly put on the strains using sterile tweezers, the strains were cultured for 24 h at 37° C., and a diameter of a bacteriostatic circle of each drug sensitive disk was recorded. This test was repeated three times, and an average value of diameters was taken. The sensitivity of the strain on the drug sensitive disk was judged according to the diameter of the bacteriostatic circle. The test results are determined according to CISI data developed by American Clinical Laboratory Standards Committee and classification and labeling of drug sensitivity.

TABLE 13

Information of drug sensitivity disks

| Abbreviation | Name | Content |
|---|---|---|
| RD | Rifampicin | 5 μg/tablet |
| TE | Tetracycline | 30 μg/tablet |
| MH | Minocycline | 30 μg/tablet |
| CN | Gentamicin | 10 μg/tablet |
| P | Penicillin | 10 μg/tablet |
| LEV | Levofloxacin | 5 μg/tablet |

TABLE 13-continued

| Information of drug sensitivity disks | | |
|---|---|---|
| Abbreviation | Name | Content |
| S | Streptomycin | 300 μg/tablet |
| AMP | Ampicillin | 10 μg/tablet |
| CTX | Cefotaxime | 30 μg/tablet |
| OX | Oxacillin | 1 μg/tablet |
| C | Chloramphenicol | 30 μg/tablet |
| FOX | Cefoxitin | 30 μg/tablet |

TABLE 14

| Drug sensitivity test of *Lacticaseibacillus paracasei* FMBL L23249 FJX | | | | | | | | | | | | |
|---|---|---|---|---|---|---|---|---|---|---|---|---|
| Strain | RD | TE | MH | CN | P | LEV | S | AMP | CTX | OX | C | FOX |
| *Lacticaseibacillus paracasei* FMBL L23249 FJX | S | S | S | R | S | S | R | S | S | R | S | R |

Note:
R: drug resistance;
I: medium sensitivity;
S: sensitivity

In order to ensure that eating probiotics is safe and reliable for a human body, the drug resistance of strains becomes an important indicator for in vitro safety evaluation of probiotic strains. It can be seen from Table 14 that the *Lacticaseibacillus paracasei* FMBL L23249 FJX is sensitive to rifampicin, tetracycline, minocycline, penicillin, levofloxacin, ampicillin, cefotaxime and chloramphenicol, and is resistant to gentamicin, streptomycin, oxacillin and cefoxitin.

4. Determination of Antioxidant Ability

The cultured bacterial solution was centrifuged (10000 rpm, 10 min, and 4° C.) to collect thalli, and the thalli were washed three times with a PBS buffer solution and then prepared into a bacterial suspension. A cell-free supernatant is a supernatant obtained by filtration via a 0.22 μm microporous filter membrane.

(1) Determination of an Ability to Clear Away Diphenyltrinitrophenylhydrazine (DPPH) Free Radical A 0.2 mM DPPH-methanol solution was prepared, and a supernatant or bacterial suspension and the 0.2 mM DPPH-methanol solution was sufficiently and evenly mixed and then reacted for 60 min in the dark. The OD517 nm value of the supernatant was measured. Three groups of repeated experiments were set.

$$DPPH \text{ clearance rate}(\%) = \left(1 - \frac{D_1 - D_2}{D_0}\right) \times 100\%$$

In the formula, D0: an absorbance of a 1 mL PBS buffer solution at OD517 nm; D1: a light absorption value of a 1 mL sample solution+1 mL DPPH-methanol solution at 517 nm; and D2: a light absorption value of a 1 mL sample solution+1 mL absolute methanol.

(2) Determination of an Ability to Clear Away ABTS

A 7 mmol/L ABTS working solution was prepared: 15 mL of 3.8 g/L ABTS solution (prepared with deionized water) prepared was correctly weighed and added into 0.264 mL of potassium sulfate aqueous solution (a molar concentration was 140 mmol/L) to be evenly mixed, and then the obtained mixed solution was placed for 12-16 h at room temperature in the dark. The working solution was adjusted to OD734 nm=0.7±0.02 using absolute ethanol, a to-be-detected sample was evenly mixed with the ABTS working solution whose concentration was adjusted in a ratio of 1:6 and then placed for 30 min at room temperature, and then an absorbance was measured at 734 nm. Three groups of repeated experiments were set.

$$ABTS \text{ clearance rate}(\%) = \left(1 - \frac{A_C - A}{A_C}\right) \times 100\%$$

In the formula, Ac: a light absorption value of equal volume of water; A: a light absorption value of a sample solution.

TABLE 15

| Antioxidant ability of *Lacticaseibacillus paracasei* FMBL L23249 FJX | | | | |
|---|---|---|---|---|
| | DPPH free radical clearance rate | | ABTS free radical clearance rate | |
| | Supernatant | Bacterial suspension | Supernatant | Bacterial suspension |
| *Lacticaseibacillus paracasei* FMBL L23249 FJX | 4.99 ± 0.88 | 47.46 ± 2.55 | 90.07 ± 0.04 | 23.17 ± 0.36 |

It can be seen from Table 15 that *Lacticaseibacillus paracasei* FMBL L23249 FJX has a relatively good ability to clear away DPPH and ABTS free radicals, the ability to clear away DPPH free radicals is manifested as bacterial suspension>supernatant, and the ability to clear away ABTS is manifested as bacterial suspension>supernatant.

In the following embodiments, the *Lacticaseibacillus paracasei* FMBL L23249 FJX was prepared into different types of microbial inoculums or food by the inventor.

Application Embodiment 1: Preparation of *Lacticaseibacillus paracasei* FMBL L23249 FJX Microbial Inoculum Preparation of a culture medium: a culture medium containing 20 gL of glucose, 8 g/L of beef extract, 10 g/L of yeast extract, 9 g/L of NaCl, 1 mL/L of Tween 80, 2 g/L of $K_2HPO_4$, 5 g/L of sodium acetate, 2 g of diammonium hydrogen citrate, 0.58 g of $MgSO_4 \cdot 7H_2O$ and 0.25 g of $MnSO_4 \cdot 4H_2O$ was prepared by using water and culture medium raw materials and adjusting the pH to 6.8.

Preparation of a protecting agent: a protecting agent containing 120 g/L of skim milk powder, 20 mL/L of glycerinum, 22 g/L of maltodextrin, 60 g/L of trehalose and 22 g/L of galacto-oligosaccharides was prepared by using water and protecting agent raw materials.

The *Lacticaseibacillus paracasei* FMBL L23249 FJX was inoculated into the above culture medium that was sterilized for 15 min at the temperature of 115° C. in an inoculation amount of 2%; the culture medium contains 20 g/L of glucose, 8 g/L of beef extract, 10 g/L of yeast extract, 9 g/L of NaCl, 1 mL/L of Tween 80, 2 g/L of $K_2HPO_4$, 5 g/L of sodium acetate, 2 g of diammonium hydrogen citrate, 0.58 g of $MgSO_4 \cdot 7H_2O$ and 0.25 g of $MnSO_4 \cdot 4H_2O$, and the pH was adjusted to 6.8. The *Lacticaseibacillus paracasei* FMBL L23249 FJX was cultured for 24 h at 37° C., washed twice with a PBS buffer solution at pH 7.2, and then re-suspended using the protecting agent so that the concentration of $10^{11}$ CFU/mL was reached. The protecting agent contains 120 g/L of skim milk powder, 20 mL/L of glycerinum, 22 g/L of maltodextrin, 60 g/L of trehalose and 22 g/L of galacto-oligosaccharides. Subsequently, the suspension was pre-cultured for 60 min at the temperature of 37° C. and then subjected to freeze drying to obtain the *Lacticaseibacillus paracasei* FMBL L23249 FJX microbial inoculum.

Application Embodiment 2: Preparation of Fermented Milk Using *Lacticaseibacillus paracasei* FMBL L23249 FJX Sugar was added into fresh milk to be dissolved, then the fresh milk with sugar was homogenized at the temperature of 60° C. under the pressure of 20 MPa and subsequently underwent preservation and sterilization for 5-8 min at the temperature of 90-95° C., the *Lacticaseibacillus paracasei* FMBL L23249 FJX of the present disclosure and a mixed bacterium consisting of commercial dry powder fermenting agents *Lacticaseibacillus bulgaricus* and *Streptococcus thermophilus* were then added in a mass ratio of 1:1:1 after the temperature decreased to 35° C., wherein the inoculation amount of the mixed bacterium was 0.03-2.0% of the weight of fresh milk, and the above materials were evenly mixed, underwent preservation and fermentation at the temperature of 37° C., coagulated and then refrigerated for 16 h at the temperature of 4° C. to obtain the fermented milk.

Application Embodiment 3: Preparation of Fruit and Vegetable Beverage Containing *Lacticaseibacillus paracasei* FMBL L23249 FJX Fresh fruits and vegetables were selected, cleaned and squeezed, and then the squeezed juice was instantly sterilized at a high temperature, immediately cooled to about 37° C. The *Lacticaseibacillus paracasei* FMBL L23249 FJX microbial inoculum prepared in the present disclosure was added, so that the concentration of the microbial inoculum reached more than $10^6$ CFU/mL. The juice added with the microbial inoculum was refrigerated and stored at the temperature of 4° C. to obtain the fruit and vegetable beverage containing the *Lacticaseibacillus paracasei* FMBL L23249 FJX viable bacteria of the present disclosure.

Application Embodiment 4: Preparation of Microcapsules and Capsule Products Containing *Lacticaseibacillus paracasei* FMBL L23249 FJX The *Lacticaseibacillus paracasei* FMBL L23249 FJX of the present disclosure was cultured for 24 h in an MRS culture medium, then centrifuged for 10 min at 4° C. under 8000 r/min, and thalli were collected, washed twice with a sterile saline solution and then resuspended using the sterile saline solution, so that the final concentration of the thalli reached $2 \times 10^{10}$ CFU/mL. The bacterial suspension was added into a solution containing 2.5% sodium alginate and 1% pectin, cells were uniformly dispersed into the sodium alginate solution by sufficient stirring, then the mixed solution was squeezed into a solidification solution containing 2% calcium chloride and chitosan to form colloidal particles, the formed colloidal particles were subjected to static solidification for 30 min, filtered and collected, the collected colloidal particles were subjected to freeze drying to obtain the microcapsules containing the *Lacticaseibacillus paracasei* FMBL L23249 FJX of the present disclosure, wherein the microcapsule had a particle size of 1.93-2.11 mm, an embedding rate of ≥93.16% and a strain viability of ≥92.57%, and had the characteristics of resisting simulated gastrointestinal fluid and cold and heat stress. The microcapsules were put into pharmaceutical capsules that were commercially available at present to obtain the capsule products.

Application Embodiment 5: Preparation of Plant Milk Containing *Lacticaseibacillus paracasei* FMBL L23249 FJX by Utilizing *Lacticaseibacillus paracasei* FMBL L23249 FJX Raw materials such as soybeans, almonds and almonds were respectively soaked for 2 h at the temperature of 80° C. After peeling, soaking water was removed. The above soaked raw materials were subjected to pulp grinding by adding boiling water, and the ground pulp was then preserved at 80-85° C. for 12-15 min. The obtained pulp was filtered via a 200-mesh sieve to remove slag, then the pulp without slag was boiled, subsequently centrifuged to remove solid matters to obtain a supernatant, the obtained supernatant was cooled to about 37° C., and then the *Lacticaseibacillus paracasei* FMBL L23249 FJX of the present disclosure was added into the cooled supernatant so that the concentration of the *Lacticaseibacillus paracasei* FMBL L23249 FJX reached more than $10^6$ CFU/mL, then the supernatant added with the *Lacticaseibacillus paracasei* FMBL L23249 FJX was refrigerated and stored at the temperature of 4° C. to obtain the plant milk containing the *Lacticaseibacillus paracasei* FMBL L23249 FJX viable bacteria.

Application Embodiment 6: Preparation of Probiotic Milk Tablet Containing *Lacticaseibacillus paracasei* FMBL L23249 FJX by Utilizing *Lacticaseibacillus paracasei* FMBL L23249 FJX 5.96 weight parts of *Lacticaseibacillus paracasei* FMBL L23249 FJX microbial inoculum prepared by using a freeze-drying method, 65.0 weight parts of whole milk powders, 7.92 weight parts of white granulated sugar, 2.5 weight parts of magnesium stearate, 18.0 weight parts of skimmed milk powders and 1.0 weight part of water were respectively weighed and mixed, and prepared into wet particles by using a conventional method, and then the above obtained wet particles were compressed into tablets by using a tablet press and dried in a drying machine, followed by packaging to obtain the probiotic milk tablet.

In conclusion, the present disclosure provides a *Lactiaseibacillus paracasei* FMBL L23249 FJX that is suitable for *Cicer arietinum L.* fermentation, wherein, the viable count of the *Lacticaseibacillus paracasei* FMBL L23249 FJX after 8 h of fermentation reaches 8.79±0.01 1 g (CFU/mL), and the viable count of the *Lacticaseibacillus paracasei* FMBL L23249 FJX after 12 h of fermentation is balanced as 9.17±0.01 1 g (CFU/mL); the *Lacticaseibacillus paracasei* FMBL L23249 FJX is capable of achieving rapid proliferation by efficiently utilizing the *Cicer arietinum L.* leach liquor. After 16 h of fermentation, the *Lacticaseibacillus paracasei* FMBL L23249 FJX has a pH value of 3.76 and a titratable acidity of 56 T°; and the *Lacticaseibacillus paracasei* FMBL L23249 FJX is more suitable for a *Cicer arietinum L.* leach liquor system. The viable count of the *Lacticaseibacillus paracasei* FMBL L23249 FJX after 12 h of fermentation reaches 9.17±0.01 1 g (CFU/mL), the viable count of the *Lacticaseibacillus paracasei* FMBL L23249 FJX in the *Cicer arietinum L.* leach liquor after storage for 12 h at 4° C. is still maintained as more than 8.32±0.03 1 g (CFU/mL), and therefore the *Lacticaseibacillus paracasei* FMBL L23249 FJX is suitable for preparing *Cicer arietinum L.* yogurt; also provided is use of the *Lacticaseibacillus paracasei* FMBL L23249 FJX in heavy metal adsorption or in the preparation of drugs, food, health products or cosmetics for heavy metal poisoning, the *Lacticaseibacillus paracasei* FMBL L23249 FJX has high adsorptivity on heavy metals lead and cadmium, i.e., the lead adsorption rate is as high as 99.87%, and the cadmium adsorption rate is 82.74%; the *Lacticaseibacillus paracasei* FMBL L23249 FJX has good acid and bile salt resistance, drug resistance, self aggregation and hydrophobicity; the strain has an inhibitory effect on enteropathogenic *Escherichia coil* (10411), enterotoxigenic *Escherichia coli* (10421), enterotoxigenic *Escherichia coli* (21530), *Salmonella typhimurium* (10420) and *Salmonella enteritidis* (SM1); furthermore, the *Lacticaseibacillus paracasei* FMBL L23249 FJX is resistant to gentamicin, streptomycin, oxacillin and cefoxitin; the *Lacticaseibacillus paracasei* FMBL L23249 FJX has an antioxidant ability; the *Lacticaseibacillus paracasei* FMBL L23249 FJX is used for preparing adsorbents for high adsorption of heavy metals lead and cadmium, and drugs, fermented food, health products, food additives and feeds or microbial formulations and the like for relieving lead and/or cadmium toxicity and inhibiting pathogenic bacteria and the like, and therefore has wide application prospects.

What is claimed is:

1. A microbial inoculum, comprising a *Lacticaseibacillus paracasei* strain FMBL L23249 FJX and a protecting agent, wherein the *Lacticaseibacillus paracasei* strain FMBL L23249 FJX is deposited with the China Center for Type Culture Collection (CCTCC) under accession number CCTCC NO: M 20231097, and wherein the microbial inoculum is freeze-dried.

2. A dairy product, which is prepared by using the microbial inoculum according to claim 1.

* * * * *